(12) United States Patent
Holt

(10) Patent No.: US 9,149,789 B2
(45) Date of Patent: Oct. 6, 2015

(54) DISPERSIONS OF SUPERABSORBENT POLYMERS, PROCESSING THEREOF AND ARTICLES FORMED FROM THE DISPERSIONS

(71) Applicant: PSMG, LLC, Woodstock, GA (US)

(72) Inventor: Jason Holt, Ball Ground, GA (US)

(73) Assignee: PSMG, LLC, Woodstock, GA (US)

( * ) Notice: Subject to any disclaimer, the term of this patent is extended or adjusted under 35 U.S.C. 154(b) by 0 days.

(21) Appl. No.: 14/171,395

(22) Filed: Feb. 3, 2014

(65) Prior Publication Data

US 2015/0217269 A1 Aug. 6, 2015

(51) Int. Cl.
*B01J 20/26* (2006.01)
*B01J 20/32* (2006.01)

(52) U.S. Cl.
CPC ............ *B01J 20/261* (2013.01); *B01J 20/3287* (2013.01); *B01J 2220/445* (2013.01); *B01J 2220/68* (2013.01)

(58) Field of Classification Search
CPC ............... G21F 9/00; G21F 9/16; A62D 3/33; B01J 20/26
USPC ........................ 588/11, 12, 412, 315; 502/402
See application file for complete search history.

(56) References Cited

U.S. PATENT DOCUMENTS

| | | | |
|---|---|---|---|
| 4,295,987 A | 10/1981 | Parks | |
| 5,676,660 A | 10/1997 | Mukaida et al. | |
| 5,817,713 A | 10/1998 | Pappas et al. | |
| 6,013,325 A | 1/2000 | Houben et al. | |
| 6,043,311 A | 3/2000 | Houben et al. | |
| 6,380,298 B2 | 4/2002 | Flautt et al. | |
| 6,540,853 B1 | 4/2003 | Suzuki et al. | |
| 7,488,541 B2 | 2/2009 | Ahmed et al. | |
| 8,338,660 B2 | 12/2012 | Gagliardi et al. | |
| 8,506,755 B2 | 8/2013 | Soerens et al. | |
| 2004/0142020 A1 | 7/2004 | Jones et al. | |
| 2008/0032014 A1 | 2/2008 | Frenz et al. | |
| 2008/0103468 A1 | 5/2008 | Elfsberg et al. | |
| 2011/0250148 A1 | 10/2011 | Mateu et al. | |

FOREIGN PATENT DOCUMENTS

WO 2012/169966 A1 12/2012
WO 2013/033391 A1 3/2013

OTHER PUBLICATIONS

Carbowax Polyethylene Glycols brochure, Dow Chemical Company, Oct. 2011, 12 pages.
International search report and written opinion for international application No. PCT/US2015/013292 dated May 6, 2015 (10 pages).

*Primary Examiner* — Edward Johnson
(74) *Attorney, Agent, or Firm* — Dardi & Herbert, PLLC; Peter S. Dardi; Kayla J. Fossen

(57) ABSTRACT

Dispersions of superabsorbent polymers are described comprising blends of polyols and super absorbent polymer. Products comprising deposits formed from such dispersions are also described. Suitable polyols can include, for example, polyethylene glycol. The dispersions can be flowed onto an absorbent sheet to form a deposit (sheeted SAP), which in some embodiments can be along a fraction of the sheet surface. Generally, the deposits are dried through a wicking process in which the polyol is wicked away from the superabsorbent polymer. The sheeted SAP can be incorporated into a final product with the deposit secured within the product. The dispersion allows for selective placement of superabsorbent polymer onto an absorbent sheet and/or in a final product. Embodiments based on coated yarns and the like are also presented.

24 Claims, 11 Drawing Sheets

DISPERSIONS OF SUPERABSORBENT POLYMERS, PROCESSING THEREOF AND ARTICLES FORMED FROM THE DISPERSIONS

FIELD OF THE INVENTION

The invention relates to dispersions of superabsorbent polymers and methods for the deposition of superabsorbent polymers from the dispersion. The invention further relates to articles formed from deposits of superabsorbent polymers.

BACKGROUND OF THE INVENTION

Superabsorbent polymer has a wide variety of uses ranging from baby diapers to soil remediation. Superabsorbent polymers are now commonly made from the polymerization of acrylic acid blended with sodium hydroxide in the presence of an initiator to form a poly-acrylic acid sodium salt (sometimes referred to as sodium polyacrylate). This polymer is the most common type of superabsorbent polymer made in the world today. The majority of superabsorbent polymer applications involve a "sprinkling" or layering technique of superabsorbent polymer powder onto a fluff pulp structure. The fluff pulp structure is then further treated by lamination, encapsulation, compressing and converting into various cut widths and lengths. The function of superabsorbent polymer relies upon a discrete particle that absorbs fluid many times its own weight.

SUMMARY OF THE INVENTION

In the first aspect, the invention pertains to a blend comprising a superabsorbent polymer (SAP) dispersed in a matrix of at least about 25 weight percent polyol that is liquid at or above 65° C. Generally, the blend comprises at least about 85 weight percent of SAP and polyethylene glycol (PEG) combined.

In further aspects, the invention pertains to a method of making a water absorbent article comprising flowing a water absorbent composition onto an absorbent sheet along a surface at a selected location to form a deposit along a fraction of the sheet surface. Generally, the water absorbent composition comprises at least about 5 weight percent super absorbent polymer and at least about 25 weight percent polyol, and the combined superabsorbent polymer and polyol makes up at least 85 weight percent of the water absorbent composition.

In other aspects, the invention pertains to a water absorbent product comprising a first sheet having a top surface, a second sheet having a bottom surface oriented toward the top surface of the first sheet, and a water absorbent composition comprising superabsorbent polymer localized to cover a portion of the second sheet, secured between the first sheet and the second sheet and in contact with the top surface and the bottom surface. A seam is formed between the top surface and the bottom surface to form a sealed enclosure that encloses the water absorbent deposit. Generally, the water absorbent composition comprises at least about 75 weight percent superabsorbent polymer and has a water absorption capacity of at least about 4 grams of water per gram of composition.

DETAILED DESCRIPTION OF THE INVENTION

Figure 1:
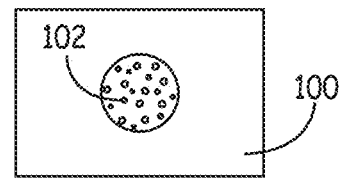
FIG. 1 is a schematic drawing depicting sheeted SAP with a specifically placed SAP deposit on an absorbent sheet.

Improved processing of superabsorbent polymers provide for the convenient formation of polymer deposits using a dispersion of the polymer to provide the ability to form a localized deposit with selected dimensions. In particular, the dispersions can be formed with polyalcohols (polyols), for example, polyether polyols such as polyethylene glycol, which generally do not dissolve superabsorbent polymers and are not absorbed aggressively by the superabsorbent polymers. Since the superabsorbent polymer does not aggressively absorb the liquid composition, the polyether polyol or other polyol can be wicked away from the superabsorbent polymer to substantially remove the liquid from the polymer. The suberabsorbent polymer can then exhibit good water absorption qualities without interference from an oily or waxy polyol. In contrast with traditional air blown techniques for delivery of a superabsorbent polymer, dispersion based delivery as described herein can be used to provide a local polymer deposit without an adhesive and a thicker deposit while providing the ability to provide confinement of the superabsorbent polymer along a sheet so that articles can be formed without undesired release of the polymer during processing. The dispersion of superabsorbent polymer can also be coated onto yarn or thread to provide an absorbent coating onto the yarn, and the coated yarn can be used to provide absorbent properties with a structure provided by the yarn. The processing approaches are suitable for commercial scale production of a range of consumer products.

The dispersion compositions for the deposition process generally comprise particles of superabsorbent polymer dispersed in a polyol liquid, e.g., polyether polyols, optionally along with minor amounts of additional additives. The concentration of polymer can be selected to achieve desired properties of the dispersion. In some embodiments, the polyether polyols can be highly viscous or solid at room temperature such that some heating can be used to achieve the desired flow properties. For the purposes of the discussion herein, a polyol liquid has a melting point under 65° C. unless indicated otherwise. As described further below, the polyether polyols can be selected to achieve desired properties of the finished product. The viscosity and other properties of the dispersion can be selected for consistency with the desired processing and deposition approach. The superabsorbent polymers generally do not dissolve in any liquid, but they absorb large amounts of aqueous liquids in a swelled mass. While the superabsorbent polymers disperse effectively in the polyols, the polymers do not swell excessively with the liquid polyols.

A superabsorbent polymer (SAP) is a polymer that is insoluble in water and generally absorbs at least 5 times it weight in aqueous solution with 0.9 weight percent sodium chloride. Superabsorbent polymers are generally granular or particulate on a submillimeter scale. The polymers are generally crosslinked and are capable of absorbing large amounts of aqueous liquids and body fluids and of retaining them under a certain pressure. SAPs are used, among other things, as an absorbing compound for baby diapers, in protecting power and communication cables, in agriculture for use in increasing the capability of soil to retain moistures and nutrients, and in the hygienic packaging of food products with absorbent pads. SAPs are known and are commercially available in the form of powders, e.g., under the designation of FAVOR® or CABLOC® or AQUA KEEP™. The polymer chain, in the presence of water or other aqueous liquid, expands as it absorbs more liquid, forming a gel. As such, SAPs swell upon exposure to water, and in some embodiments, are capable of absorbing up to 500 times their weight in water. Suitable superabsorbent polymers are generally lightly or moderately crosslinked with polar functional groups. Various suitable polymers are summarized further below, and currently popular commercial SAPs include, for example, crosslinked polyacrylic acids, and copolymers thereof that can be neutralized with sodium hydroxide or potassium hydroxide. The polymers generally include water binding groups, for example carboxylic acid groups. The salt ions of the acrylate-based polymers, as used in the present invention, are located at the carboxylic acid groups pendant from the polymer carbon backbone.

SAPs may be in the various forms of powders, particles, granules, film, sols suspension gels, non-woven fabrics, flakes, pellets or short needles. For the formation of the suspensions described herein, the superabsorbent polymers are generally in powder form or the like, although other forms may be suitable if deposition using a selected technique is possible. SAPs may be any of various superabsorbent polymers having an average particle size of about 500 microns, where particle size is measured along the largest dimension of the particle. A selected average particle size may be smaller or larger depending upon the particular application for the coating. For some applications, SAPs have been used in powder form or in a composite form in which SAP particles are blended with fine fibers and then entrapped within a fibrous mat. As described herein, the SAP dispersions can be coated onto yarn or fibers, and the resulting coated yarn or fibers can be similarly formed into mats or other similar structures for incorporation into products.

The dispersion of superabsorbent polymer in a polyol liquid can be deposited using any reasonable approach. For example, the dispersion can be sprayed, screen printed, extruded, painted, gravure printed, or the like. Also, an absorbent sheet, yarn or fibers can be dipped, immersed or conveyed through the SAP dispersion to coat the sheet or yarn. Generally, spraying suggests a lower viscosity, while screen printing suggests more a paste consistency, and a person of ordinary skill in the art can adjust the dispersion suitably for a selected deposition approach. While the dispersions can be deposited essentially uniformly across a sheet surface, the dispersions can be deposited over a selected portion of a surface. For example, the deposits can be placed over most of the surface with an edge exclusion to provide for sealing of the deposited, or in some embodiments, the deposits can be placed in a pattern to provide alternative appearance or feel or absorption performance of the product for a particular amount of superabsorbent polymer. The polyether polyol generally provides a cohesive deposit upon deposition without clumping so that a desired thickness of superabsorbent polymer within reasonable ranges can be placed in a stable form on a surface of a sheet. The cohesive deposit generally does not easily separate from the deposited location so that handling is generally not problematic during the formation of the finished product. The superabsorbent polymer can be dried, i.e., most of the polyol liquid can be wicked away from the deposited superabsorbent polymer. The dried superabsorbent polymer can exhibit good water absorbing abilities, which can roughly approximating the superabsorbent polymer as added to form the dispersion. The deposit can then effectively swell when placed in contact with an aqueous solution, such as water, bodily fluid, food run off, soil run off or the like.

The dispersion can be deposited onto an absorbent sheet, such as a tissue. The absorbent sheet can have greater affinity for the polyol liquid than the affinity of the superabsorbent polymer for the polyol liquid. Thus, the absorbent sheet can wick or drain the liquid polyether polyol from the deposit. The removal of a substantial amount of the polyol liquid, e.g., polyether polyol, through the draining or wicking process results in a relatively dry superabsorbent polymer and an absorbent sheet wetted with the polyol liquid. The wicking process is demonstrated in the Examples below. At equilibrium there may be some polyol liquid associated with the superabsorbent polymer, but the amount should be essentially inconsequential for appropriately selected absorbent sheets. Tissue paper or the like can be suitable for use as the absorbent sheet with the formation of a dried superabsorbent polymer deposit. Heat may or may not be applied during the process of forming the dried superabsorbent polymer to either drive the process if the polyol liquid melts at a temperature above room temperature or to speed the proceed through the increased mobility of the polyol liquid.

Following the drying of the superabsorbent polymer, the absorbent sheet can be somewhat oily or waxy depending on the properties of the polyol. For example, ethylene glycol and PEG 100 can have an oily consistency, while PEG 1000 can have a waxy feel. The presence of the polyether polyol can reduce the hydrophobicity of the absorbent sheet, which may be useful to facilitate the wetting of the superabsorbent polymer with water or other aqueous solution during use. The dried superabsorbent polymer generally has an absorbency of aqueous solutions of at least about 50 percent of the absorbing ability of the unprocessed superabsorbent polymer component. Thus, the wetted absorbent sheet along with the dried deposit of superabsorbent polymer generally are incorporated together into the product. The superabsorbent polymer generally is encapsulated within a cover sheet to stabilize the polymer within the article such that the superabsorbent polymer does not significantly migrate from the deposition location. Multiple layers of various components of the structure can be included as desired in the product. For example, the absorbent sheet can be covered with an additional layer such that the absorbent sheet is not along the exterior of the final product.

In contrast with the fluid deposition approaches described herein, a traditional sprinkling or layering process generally applies superabsorbent polymer to the entire length and width of an absorbent core structure formed on a support sheet. Full application of superabsorbent polymer to the absorbent core places superabsorbent polymer in the edges of the structure where it may be more difficult to contain and may be less useful in the product than the amount of superabsorbent polymer at the center section or other sections of the absorbent core. In applications where superabsorbent polymer is used in food packaging, the edges of an air-laid structure (e.g., soaker pads) containing superabsorbent polymer involve appropriate containment to prevent gel particles from contaminating the food product. The containment or pouch pad requirement for food packaging can substantially raise costs over that of a standard superabsorbent polymer containing pad, a cellulose fluff pulp (pouch sealed) that contains granular SAP. The pad can have unwoven perforated polymer films that let water enter but the holes are too small to allow the polymer to pass. In the structures described herein, the tissue may replace the cellulose fluff pulp. Other issues associated with superabsorbent polymer processing, such as efficient distribution of the polymer, gel blocking, dust, and the like, may be improved with the fluid processing described herein.

Superabsorbent polymer particles that are too small tend to clump in regions of fluff pulp or air laid structures, and in use clumps can "gel block" aqueous fluid, i.e., slow fluid migration, from reaching other less hydrated particles of superabsorbent polymer in adjacent the localize regions of the absorbent structure. Gel blocking can result in superabsorbent polymer not being fully utilized as intended. Large superabsorbent polymer particles are much slower to absorb aqueous liquid than smaller superabsorbent polymer particles and can result in absorbent product leakage. The process approaches described herein can effectively deposit small superabsorbent polymer particles with less clumping such that a more effective product can be formed with a given amount of superabsorbent polymer.

The fluid based processing described herein provides a superabsorbent polymer powder in a non-solvent carrier liquid, i.e., a dispersion in which the superabsorbent polymer does not dissolve or significantly swell, although it can disperse well. A superabsorbent polymer dispersion allows for direct placement of superabsorbent polymer particles onto absorbent cores with reasonable precision. Controlled placement of superabsorbent polymer offers the ability to concentrate superabsorbent polymer placement into regions of an absorbent article with the highest demand for fluid uptake. Other applications may include applying the superabsorbent polymer dispersions to non-airlaid structures such as wet laid paper, synthetic fiber webs etc as a finish coating to provide increased fluid absorbency or water blocking characteristics. Other applications may include, for example, bio-medical absorbency without the problems associated with dry powder gel blocking. Food packaging "soaker pads" will benefit from precise superabsorbent polymer dispersion placement whereas superabsorbent polymer would not be present at the edges of the pad, in direct contact with food.

The formation of a structured localized deposit comprising a superabsorbent polymer is described in U.S. Pat. No. 8,338,660 to Gagliardi et al. ("the '660 patent), entitled Absorbent Article Comprising an Absorbent Element Comprising a Liquid Absorbent Thermoplastic Composition," incorporated herein by reference. While the liquid absorbent composition in the '660 patent comprises superabsorbent polymer, the overall composition includes significant additional components, such as a thermoplastic polymer, that remain associated with the composition in the final article. Thus, while deposits can be shaped in the product using these thermoplastic compositions, the composition generally have significantly lower water absorbing capacity than the superabsorbent polymers. The compositions described herein provide the ability to deposit the absorbent material in a shaped configuration without significantly sacrificing the absorbing ability of the absorbent composition in the final product.

The structures incorporating encapsulated superabsorbent polymer can be incorporated into a variety of products that provide significant water uptake properties. The polyol liquids are generally non-toxic or have very low toxicity, such that reasonable levels of contact with human skin, contact with food products or release into the environment is acceptable. Thus, suitable products include, for example, personal hygiene products, such as disposable diapers, wipes, feminine hygiene products, and the like, food packaging components, such as absorbent pads under meat products, industrial absorbent pads, soil remediation products, and the like.

For some desired product, the processing approaches provide for significant conveniences, and desirable articles can be conveniently formed through the processing approaches. The polyols that are introduced into the products generally are benign and can introduce some desirable properties for the product. The processing approaches can be performed in a cost effective manner for commercial application, and the processing components, including the absorbent sheet or tissue and the polyols are generally relatively inexpensive.

Fluid Compositions

The processing to form absorbent articles described herein involves the use of a dispersion of the superabsorbent polymer in a polyol liquid. The superabsorbent polymer is generally not soluble in the liquid so that dispersions can be formed with reasonable deposition properties, and the superabsorbent polymers can be "dried" through the wicking away of the liquid since the polymer does not swell with the liquid. The parameters of the dispersion can be selected to achieve desirable properties of the deposits as well as for compatibility with a selected deposition or other delivery approach. The dispersion can comprise optional additives to modify the deposits and/or the deposition properties. The components of the dispersion are mixed well to blend the components and form the dispersion, and the formation of the dispersion is discussed further in the processing section below.

The amount of polyol liquid in the dispersion can be adjusted to influence the viscosity of the dispersion and other fluid properties as well as to influence the properties of the deposit and the subsequent drying process. The nature of the polyol itself also influences the properties as described further below. The dispersion generally comprise from about 10 weight percent polyols to about 95 weight percent polyols, in further embodiments from about 20 weight percent to about 90 weight percent and in additional embodiments from about 25 weight percent to about 85 weight percent polyols. Correspondingly, the dispersion generally comprises from about 5 weight percent to about 85 weight percent superabsorbent polymer, in further embodiments from about 10 weight percent to about 75 weight percent and in additional embodiments from about 15 weight percent to about 65 weight percent superabsorbent polymer. The dispersion can optionally comprise no more than about 20 weight percent additives, in further embodiments from about 0.5 weight percent to about 20 weight percent, in some embodiments from about 1 weight percent to about 18 weight percent and in additional embodiments from about 2 weight percent to about 15 weight percent additives. Additives refer to a combination of one or more optional components of the dispersion other than the superabsorbent polymer and the polyols. Suitable additives include, for example, fibers, other polymer solids, other liquids, antimicrobials, viscosity modifiers, surfactants, coloring agents, fragrances, or the like, or combinations thereof. Additives may or may not remain with the deposited superabsorbent polymer following drying. A person of ordinary skill in the art will recognize that additional ranges of dispersion compositions within the explicit ranges above are contemplated and are within the present disclosure.

The polyol liquid can be polymeric or non-polymeric compositions or mixtures thereof. For example, the polyol liquid can comprise, for example, ethylene glycol, propylene glycol, glycerol, blends thereof or the like. In some embodiments, the liquid of the suspension comprises a liquid polyether polyol, e.g., diol or triol, with oxyethylene repeat units along the polymer backbone, which generally have moderate molecular weights, such as polyethylene glycol (PEG, HO—$(CH_2$—$CH_2$—$O$—$)_n$H), propylene glycol (PPG, HO—$(CH_2$—$CHCH_3$—$O$—$)_n$H), copolymers thereof or a mixture thereof (PEG/PPG) as the primary component or only component. PEG and PPG are ethers with two terminal hydroxyl groups and can be moderately viscous compositions, which influences the viscosity of the suspension. Glyceryl ether polymers are commercial polymers with PEG or PPG reacted with a glycerine molecule to form an ether linkage with the resulting molecule having three terminal hydroxyl groups. (Dow®, PT-series of polymers).

Polyethylene oxide can be represented by the formula —$(—O$—$CH_2$—$CH_2)_n$—OH, where n refers to the degree of polymerization, and for high molecular weight polymers, n is large. Suitable polymers can be linear or branched. Polyethylene glycol (PEG), polyethylene oxide (PEO), or poly(oxyethylene) (POE) refers to an oligomer or polymer of ethylene oxide. The three names are chemically synonymous, but historically PEG has tended to refer to oligomers and polymers with a molecular mass below 20,000 g/mol, PEO to polymers with a molecular mass above 20,000 g/mol, and POE to a polymer of any molecular mass. The nature of the polyether polyol polymer can be characterized by the average molecular weight. PEG compositions can be liquids or low melting solids, depending on the molecular weights of the polymer. PEG 400 generally refers to a PEG formulation with an average molecular weight between 380 g/mole and 420 g/mole. PEG 400 is commercially available, for example, as Dow CARBOWAX™ PEG 400. PEG 600 generally refers to a PEG formulation with an average molecular weight between 570 g/mole and 630 g/mole. Above a molecular weight of roughly 800 g/mole, PEG can be a waxy paste like material at room temperature. In some embodiments, PEG and/or other polyether polyol with an average molecular weight of no more than 800 g/mol can be desirable in the dispersion for flow properties, although as noted below heat can be applied to facilitate the flow and processing generally. Commercial PEG and other polyether polyols can have mixtures of polymers with different degrees of polymerization. Ethylene glycol dimers have a molecular weight of about 104 g/mol, which corresponds with PEG 100. In further embodiments, polyether polyols in the dispersion can have average molecular weights from about 100 g/mol to about 600 g/mol and in other embodiments from about 100 g/mol to about 400 g/mol. In some embodiments, the dispersion can be deposited with modest heating, as described further below, and in these embodiments, the average molecular weight of a polyether polyol can be from about 800 g/mol to about 8000 g/mol, in further embodiments from about 900 g/mol to about 5000 g/mol and in additional embodiments from about 900 g/mol to about 4000 g/mol. A person of ordinary skill in the art will recognize that additional ranges of average molecular weights within the explicit ranges above are contemplated and are within the present disclosure. In general, any reasonable blend of polyols can be used to form the dispersion to achieve desired dispersion properties.

Commercial superabsorbent polymers can be salts of polyacrylic acid, such as sodium salts, potassium salts and/or ammonium salts. Other acrylic acid, methacrylic acid, other carboxylic acid functional groups and similar polymers and their salts that have superabsorbent properties with respect to water absorption are contemplated. However, other polymers can exhibit superabsorbent properties with respect to aqueous solutions, such as carboxymethyl cellulose, a hydrolysis product of starch-acrylonitrile grafted copolymer, a partially crosslinked polyacrylamide, vinyl polymers with sulfonic acid functional groups (e.g. poly 2-acrylamido-2-methyl propane sulfonic acid) or phosphoric acid functional groups, vinyl polymers with carboxylic acid anhydrides, such as maleic anhydride, a isobutylene maleic acid copolymer and the like. Superabsorbent polymers are discussed further in U.S. Pat. No. 8,506,755 to Soerens et al., entitled "Creped Tissue Product with Enhanced Retention Capability," incorporated herein by reference. Similar graft or block copolymers can be used, such as starch graft copolymers with the above noted vinyl polymers, such as the polyacrylic acid polymer salts, to achieve desired overall polymer properties. In particular, the polymeric component formed from the unsaturated, acid-containing monomers can be grafted onto other types of polymer moieties such as starch or cellulose. Suitable unsaturated acidic monomers for use in preparing the polymeric absorbent gelling materials used in this invention include those listed in U.S. Pat. No. 4,654,039 and reissued as RE 32,649, which are incorporated herein by reference. Superabsorbent polymers can be found commercially as CABLOC 80HS available form Stockhausen Inc., Greensboro, N.C.; and AQUA KEEP J-550-SF available form Sumitomo Seika Chemical Company, Ltd.

The term crosslinked used in reference to the superabsorbent polymer generally refers to any means for effectively rendering normally water-soluble materials substantially water-insoluble but swellable. While such a polymer may otherwise dissolve, a slight crosslinking present in the SAP chains used in the present invention prevents them from completely dissolving. Crosslinking can include, for example, physical entanglement, crystalline domains, covalent bonds, ionic complexes and associations, hydrophilic associations such as hydrogen bonding, hydrophobic associations, Van der Waals forces or combinations thereof. In some embodiments, superabsorbent polymers can comprise covalent crosslinking along with possibly other crosslinking mechanisms. Superabsorbent polymers can have internal crosslinking and/or surface crosslinking. In general, the SAP whose surface is crosslinked is high in absorbance under load (AUL) value; specifically, it has an AUL of at least 20 ml/g or higher under such load. In some embodiments, SAPs that are surface crosslinked can be uniformly dispersed in mixture mediums of organic solvents and water among organic mediums SAPs that are not surface crosslinked or difficult to surface crosslink, on the other hand, may have a narrow selection of suitable dispersion liquids as they need to be dispersed in a hydrophobic medium. SAPs that are highly crosslinked may have a lower swelling capacity than SAPs that are less highly crosslinked.

In some embodiments, the average particle size is from about 1 to about 500 microns, and the polymer is in powder form. In further embodiments the particle size can be from about 10 microns to about 250 microns, from about 25 microns to about 200 microns, or from about 30 microns to about 150 microns. A person of ordinary skill in the art will recognize that additional ranges of average particle sizes within the explicit ranges above are contemplated and are within the present disclosure. As used herein, the particle size is the largest dimension across a polymer particle. The particle sizes may influence the absorption rate for aqueous fluids, and different average particle sizes may be desirable for different applications. The particle sizes may also influence the properties of the dispersion formed with the superabsorbent polymer.

The swelling of superabsorbent polymers can be evaluated based on the weight change exhibited by the polymer upon submersion in 9% by weight sodium chloride solution in water. The SAP is weighted and then submerged for 20 minutes in the salt solution. To perform the swelling measurement superabsorbent polymer can be enveloped in webbing or porous sheeting analogous to a tea bag or placed directly in the solution and filtered to separate the polymer from the solution for weighing. The swelling is determined as the weight change, i.e., the weight of the swelled polymer minus the weight of the initial dry polymer, divided by the weight of the initial dry polymer. In general, superabsorbent polymers can have an absorption of at least about 5 times the polymer weight in aqueous solution, in further embodiments at least about 7 times, in additional embodiments from about 8 times to about 300 times and in other embodiments from about 12 times to about 250 times of absorbed aqueous solution (9 wt % saline in water) relative to the polymer weight. A person of ordinary skill in the art will recognize that additional ranges of absorption within the explicit ranges above are contemplated and are within the present disclosure. A particular article may be designed with a SAP that has an intermediate degree of swelling to conform to physical constraints on the article, and the processing approaches described herein provide for desired placement within the article.

After the SAP deposit is "dried" through a wicking process, the substantial portion of the polyol is removed from the SAP deposit. In some embodiments the dried SAP deposit comprises at least about 50 weight percent super absorbent polymer, in further embodiments at least about 75 weight percent superabsorbent polymer and in additional embodiments at least about 85 weight percently polymer. The dried SAP deposit generally can absorb at least about 4 times its weight in 9 weight percent aqueous sodium chloride solution. A person of ordinary skill in the art will recognize that additional ranges of dries SAP deposit properties within the explicit ranges above are contemplated and are within the present disclosure.

Products

As noted above, the processed superabsorbent polymers can be applied to a range of products from personal care products for consumers, products for the food service industry, landscaping products, industrial products and the like. In some embodiments, the products have in common the incorporation of sheets with the deposits of SAP along a surface of the sheet and encapsulation of the polymer within other components of the article. The articles can have multiple layers or portions thereof of the sheeted SAP deposits. In additional or alternative embodiments, the products can incorporate yarns or the like coated with the SAP dispersions, which may or may not be formed into mats. In general, the finished product has a porous surface sheet providing fluid access to the superabsorbent polymer. Examples of finished products include food packaging soaker pads, ice packs for food refrigeration, radioactive water disposal materials, fiber optic cable insulation, personal hygiene products (feminine hygiene products, adult diapers, sanitary napkins, etc.), diapers, and biomedical waste containers. The intended final use can influence the desired properties of the SAP deposit.

The superabsorbent polymer dispersion can be used to deposit the polymer onto an absorbent sheet to form sheeted SAP deposits in a structure that can be referred to as sheeted SAP. The sheeted SAP structure then forms a component of an ultimate product, although in principle the sheeted SAP can be used directly as formed. The absorbent sheet generally can be any porous sheeting that has absorption affinity for the polyols used in the dispersion of superabsorbent polymers. Suitable absorbent sheets can be made from any material that appropriately absorbs the polyols and can include, for example, tissues, generally formed from cellulose fibers, other sheeting from wood pulp fibers, fabric, cotton, or the like, or combinations thereof. The absorbent sheets can have a thickness sufficient to hold the deposits of superabsorbent polymer without ripping and to absorb sufficiently the polyols to dry the SAP deposits. Generally, the thickness can be from about 10 microns to about a millimeter, although alternative ranges within this explicit range are contemplated and part of the present disclosure. An embodiment of sheeted SAP is depicted schematically for example in FIG. 1. Sheeted SAP comprises an absorbent sheet 100 with a specifically placed SAP polymer 102. A sheeted SAP sample is also shown in the Examples.

In some embodiments, the SAP deposit covers effectively the entire the surface of the absorbent sheet, and a subsequent converting step to form the product from the sheeted SAP can provide for sealing the structure with appropriate overlap of the covering material to enclose the sheeted SAP. In some embodiments, it can be desirable to cover only a fraction of the absorbent sheet when forming the sheeted SAP to facilitate subsequent processing. Thus, the surface area of the SAP deposit on the sheeted SAP may cover from 10% to 90% of the surface area of the absorbent sheet. In some embodiments, the SAP deposit may cover from about 10% to about 75%, about 10% to about 50%, or about 15% to about 80% of the surface area of the absorbent sheet. The surface area of the deposits can be evaluated following drying of the superabsorbent polymer, although the coverage of the as deposited SAP deposit generally is similar to the coverage following drying. The selected surface area can be based on the size of the area targeted for absorptive properties as well as the amount of liquid expected to be absorbed. For some embodiments, the average thickness of the SAP deposit may be from about 0.1 mm to about 2 cm thick. In further embodiments, the average thickness of the SAP deposit may be from about 0.5 mm to about 1 cm, about 1 mm to about 9 mm, or about 1 mm to about 7.5 mm thick. A person of ordinary skill in the art will recognize that additional ranges of surface coverage and average thickness within the explicit ranges above are contemplated and are within the present disclosure.

The thickness of the SAP deposit can be relatively uniform or forming a particular shape, such as a mound. The thickness variation generally is consistent with the ultimate product. For example, some products suggest a relatively flat and uniformly thick deposit with a thickness variation over the deposit relative to the average thickness reaching generally no more than about 20 percent and in some embodiments no more than about 10 percent with a 1 millimeter edge exclusion, i.e., the outer edges of the deposit are excluded, for the evaluation of the thickness variation. A person of ordinary skill in the art will recognize that additional range of thickness variation within the explicit ranges are contemplated and are within the present disclosure. The particulate nature of the polymer and the softness of the polymer suggest that edges of the deposit are not sharp so that the thickness decreases gradually at the edges. In some embodiments, the SAP may be more mounded to provide greater absorption of aqueous liquid at a selected location such as along a centered band on the absorbent sheet. The average thickness of the SAP deposit can be selected based upon the amount of liquid expected to be absorbed as well as the required dimensions of the final product. For example, a thinner SAP deposit may be require in feminine hygiene products, as the thickness effects the comfort and aesthetic of the product. A thicker SAP deposit may be required in disposable diapers, as a larger quantity of liquid is expected to be absorbed.

The size of the sheeted SAP can be influenced by the products to be formed as well as the manufacturing process. For example, the sheet can be dispensed from a roll as an effectively continuous web for placement of SAP deposits with selected dimensions. The sheeted SAP on a continuous web can be rolled up for later use or transported for cutting and further processing into a product. As shown below in the Examples, the SAP deposits formed from the dispersions can be relatively stable on the sheets. For roll based deposition the width of the roll can be selected to fit into a finished product, and can be in some embodiments from about 1 centimeter to about five meters, in further embodiments from about 3 centimeters to about three meters and in additional embodiments from about 5 centimeters to about two meters. For embodiment not based on rolls, the sheeted SAP can have sized sheets with surface areas from about 1 $cm^2$ to about 1 $m^2$, in further embodiments from about 10 $cm^2$ to about 7500 $cm^2$ and in other embodiments from about 25 $cm^2$ to about 5000 $cm^2$. The sheet can have any reasonable shape, such as round, oval, rectangular, elliptical, parabolic, triangular, hexagonal, or the like. In general, the linear dimensions of the sheet from edge to edge through a center point of area can fall within ranges for the rolled sheet widths specified above for many products of interest. A person of ordinary skill in the art will recognize that additional ranges of linear dimensions and surface areas within the explicit ranges above are contemplated and are within the present disclosure.

For many products, the sheeted SAP can comprise a single SAP deposit covering desired dimensions. However, in other embodiments, the sheeted SAP can comprise a plurality of separated SAP deposits each with appropriately selected deposits positioning and dimensions. The number of SAP deposits in a final product may be determined by the intended use of the product. In some embodiments there may be from 2 to 20 SAP deposits, from 2 to 15, from 2 to 5, or more than 20 deposits. Uses where liquid may be expected to be coming from multiple locations may benefit from an increased number of SAP deposits. The deposits may be place so as to direct the flow of liquid or to absorb liquid in a particular location. Also, the use of multiple deposits can influence the look and or feel of the product, which can be significant for personal care or other applications, as well as to influence a possible three dimensional shape of a finished product that may have curved surfaces in use. In some embodiments, the deposits may be placed up to an edge. In additional or alternative embodiments the deposits can be placed at least about 1 mm, at least about 5 mm, or from about 1 cm to about 5 cm away on average from the edges of the porous sheet on the sheeted SAP. A person of ordinary skill in the art will recognize that additional ranges of deposit numbers and edge spacing within the explicit ranges above are contemplated and are within the present disclosure. Examples of the use of patterned absorbent materials for personal care products is described further in the '660 patent cited above, although this patent described significantly different compositions within their deposits.

The sheeted SAP generally is further processed for incorporation into a structure forming a finished product. The SAP deposits may be optionally encapsulated to prevent migration of the SAP deposit. For embodiments with a plurality of SAP deposits on the sheeted SAP, the SAP deposits may be encapsulated individually. The SAP deposits may also be encapsulated collectively. A product may comprise a single element of sheeted SAP or multiple elements of sheeted SAP. If the product comprises multiple elements of sheeted SAP, the elements can be at separate locations, stacked on top of each other, partially overlapping each other or a combination thereof. Stacks of sheeted SAP can be used to increase the absorption capabilities in the product, and the use of multiple elements of sheeted SAP at separate locations can provide for a desired overall product configuration. For example, a product can comprise 2, 3, 4, 5, 6, or more than 6 elements of sheeted SAP.

When a single element of sheeted SAP is used, each deposit may be encapsulated separately or in small groups on the single sheet. Alternatively, the entire sheet may be encapsulated with a single enclosure. When multiple sheets are used, each individual deposit may be encapsulated individually or in small groups, or each sheet containing deposits may be individually encapsulated, or more than one up to all of the sheets containing deposits may be encapsulated as a group. Suitable materials for encapsulation are permeable to aqueous liquids. In some embodiments, a combination of materials can be used to encapsulate the SAP deposits, such as a water resistant sheet and a water permeable sheet to be placed on opposite sides of the sheeted SAP. Examples of encapsulating materials include, for example, woven or non-woven cloth, paper, porous or non-porous polymer sheets, filter paper, food grade plastic, or the like or combinations thereof. The encapsulating material and/or the final product can be sealed by any appropriate method based on the materials and structure. Examples of sealing approaches include, for example, stitching, adhesive bonding (with e.g. glue, tape, or the like), heat bonding, pressure bonding, clamping, or the like or combinations thereof.

Figure 2:
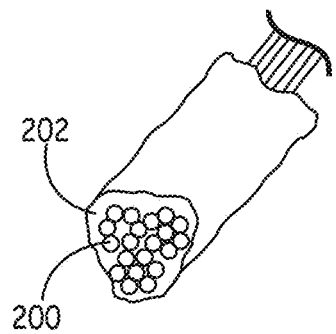
FIG. 2 is a perspective schematic view of an SAP coated yarn.
Figure 3:
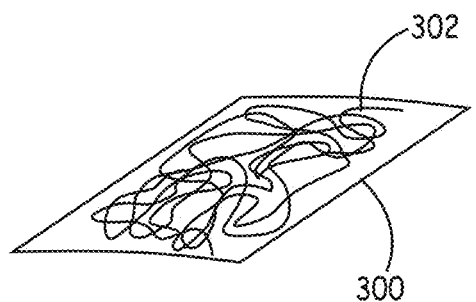
FIG. 3 is a plan view of a mat assembled from coated yarn sections.

In some embodiments, the SAP dispersions can be coated onto yarn, rope, thread or the like, which for convenience of discussion is generally referred to collectively as yarn. The coated yarn can then be woven, formed into a mat, wound or otherwise formed into a structure for incorporation into an article. Generally, the yarn can be formed from the same materials provided above for the absorbent sheet. The yarn generally can wick polyols from the deposited SAP dispersion in the same way that the absorbent sheet wicks the polyols to dry the SAP polymer. In general, any reasonable yarn dimensions can be used, but in some embodiments the yarn has a thickness of no more than about a centimeter in diameter. The yarn format can provide an alternative for providing SAP deposits to articles for convenience. The yarns can provide additional structural options for the formation of the articles. While a range of articles can be formed from the coated yarns, in some embodiments, the coated yarns can be assembled into a mat and upon drying the dried structure can have a relatively stable shape. A coated yarn fragment is shown schematically in FIG. 2 and mat assembled from coated yarn sections is shown in FIG. 3. Referring to FIG. 2 yarn fibers 200 are coated in SAP dispersion 202. FIG. 3 depicts mat 300 assembled from coated yarn sections 302.

Processing

Processing to form the absorbent articles can broadly be considered to comprise forming the superabsorbent polymer dispersions, depositing the dispersions to form sheeted SAP and incorporating the sheeted SAP into an ultimate product if different from the sheeted SAP. The respective broad steps or subcombinations thereof may or may not be performed at nearby locations. The products may then be packaged for distribution to the ultimate consumer if not consumed near the assembly location.

Forming the dispersion generally comprises the blending of the particulate SAP polymer with the dispersing liquid along with any optional additives. A suitable mixing device can be used based on the volumes and viscosity of the dispersion. The mixed dispersion can be stored, shipped or deposited without storage or shipping. Suitable containers can be glass, metal, plastic, ceramic, combinations thereof or other suitable containers. Suitable mixers can involve various mixing elements, such as paddles, auger/screw or beater, and/or sonication.

The deposition of the superabsorbent polymer dispersion can be performed using any reasonable depositions process, including, for example, spraying, painting, extruding, screen printing, gravure printing, dip coating, immersion, or the like. It is understood that any number of application methods can be used including in some embodiments a single or multiple stream application nozzle, an air assisted spray nozzle, a doctor blade, a printer, an ink roller, etc. These methods can be used individually, in plurality, or in combination to create the desired SAP placement and distribution for a given final product. The viscosity of the SAP fluid can be tailored to the chosen application method. For example, a higher viscosity SAP fluid can be applied using a stream nozzle, whereas an air assisted spray nozzle will generally require a lower viscosity SAP fluid. A SAP deposit on the sheeted SAP may be placed individually, or a plurality of deposits may be layered. One, more than 1, more than 3, or more than 5 layers from individual deposition steps may be used to form an overall deposit. After depositing the dispersion of superabsorbent polymer, the deposits dry due to wicking of the polyols from the deposits. To dry the deposits to a desired degree a reasonable period of time may pass, but the deposits may not be fully dry when further processing is performed to the sheeted SAP. In some embodiments, the sheeted SAP is dried for at least about 1 minute, in further embodiments from about 2 minutes to 12 hours, in additional embodiments from about 5 minutes to about 6 hours. A person of ordinary skill in the art will recognize that additional ranges of drying time within the explicit ranges above are contemplated and are within the present disclosure.

As noted above, it may be desirable to heat the materials to form the dispersion, to perform the deposition and/or to dry the SAP deposits. The heating can melt room temperature solid polyols as well as lower the viscosity of liquid polyols to facilitate the deposition process, speed the drying process or otherwise facilitate processing. In general, relatively modest heating can significantly alter the dispersion properties. In some embodiments, the materials can be heated to a temperature from about 30° C. to about 95° C., in further embodiments from about 35° C. to about 85° C., and in additional embodiments from about 40° C. to about 75° C. A person of ordinary skill in the art will recognize that additional ranges of temperatures within the explicit ranges above are contemplated and are within the present disclosure. Heat can be applied through any reasonable approach, such as a heating lamp, hot air blower, heating element, a hot plate, passage through an oven or other heated enclosure or any other reasonable approach based on the target temperatures.

Figure 4:
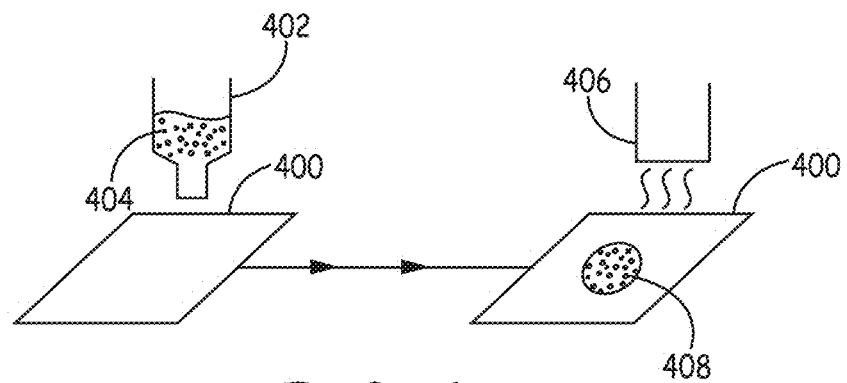
FIG. 4 is a schematic layout of a processing system with the delivery of SAP dispersion from a reservoir.
Figure 5:
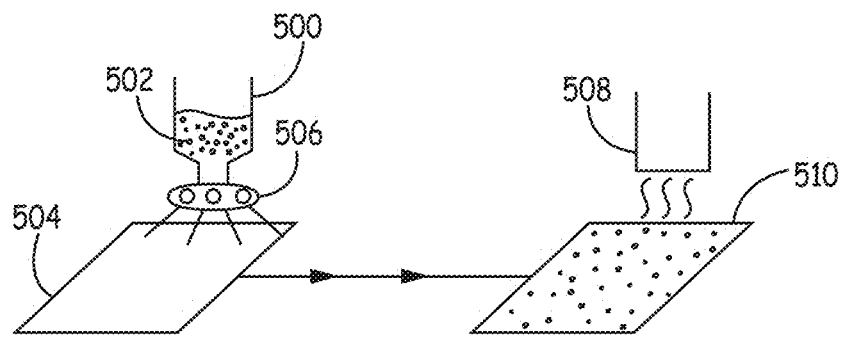
FIG. 5 is a schematic layout of a processing system with the delivery of SAP dispersion through a spray nozzle.

The processing to form the sheeted SAP comprises the deposition of the SAP dispersion on the absorbent sheet. The SAP dispersion can be deposited form a reservoir or the formation of the dispersion and deposition can be performed in a continuous process, such as the blending of the superabsorbent polymer powder with the polyols and optional additives in an extruder or the like which is blended in the extruding process and subsequently deposited in a continuous process. For example, FIG. 4 depicts a processing system with the delivery of SAP dispersion from a reservoir. Reservoir 402 containing SAP fluid 404 releases fluid 404 through a nozzle onto absorbent sheet 400. Reservoir 402 may or may not provide additional mixing, continuous and/or intermittent, of the SAP dispersion. Absorbent sheet 400 containing precisely placed SAP 408 is then optionally heated by heat source 406 to speed the drying process. Similarly, in FIG. 5, reservoir 500 is attached to spray nozzle 506 which deposits SAP fluid 502 onto absorbent sheet 504. The sheet containing SAP 510 is then optionally heated using heat source 508 to speed the drying process through the faster wicking of the polyol by the absorbent sheet. An embodiment of a resulting sheeted SAP article is shown in FIG. 1 described above. A suitable conveyor can be used to convey sheets through the processing stages for efficient handling of the sheets for processing. This system can be conveniently adapted for roll-to-roll processing in which sheet is unwound from a supply roll for delivery of sheet for SAP dispersion deposition and conveyed for further processing or for rolling onto a take up roll for subsequent use.

Figure 6:
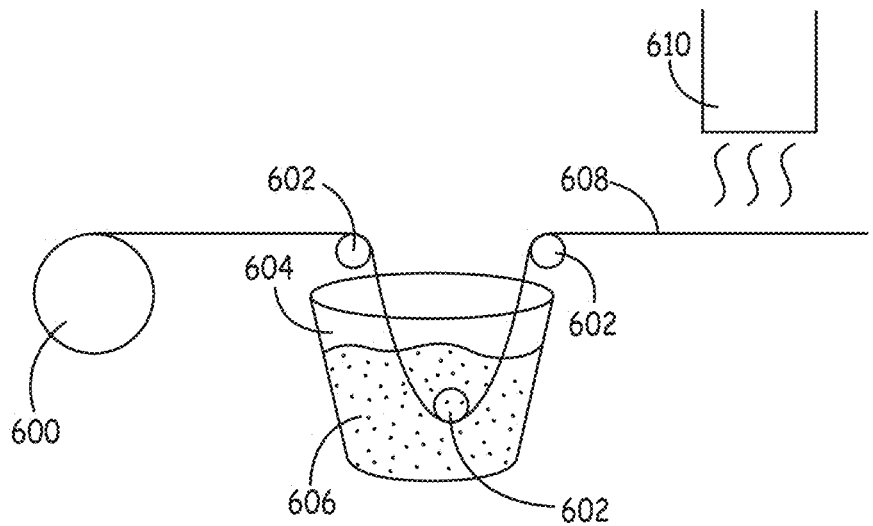
FIG. 6 is a schematic layout of a processing system with a yarn dip coated in an SAP dispersion.

Yarn can be coated with SAP dispersion using any reasonable coating technique, such as spray coating or the like. In some embodiments, a plurality of spray nozzles positioned around a conveyed yarn strand can be used to apply a roughly even coating onto the yarn as it passes by the nozzles. In further embodiments, the yarn can be dip coated to apply the SAP dispersion. The uncoated yarn can be unwound from a spool, dipped into the SAP dispersion can conveyed to an uptake spool or to a further processing section where mats or other articles are assembled from the coated yarn. Referring to FIG. 6, yarn 608 is drawn off of roll 600, along directional rollers 602 into the reservoir 604 and through SAP dispersion 606. The coated yarn dries the SAP with the passage of time as the yarn absorbs the polyol from the superabsorbent polymer or is assisted by optional heating 610.

Figures 7, 8:
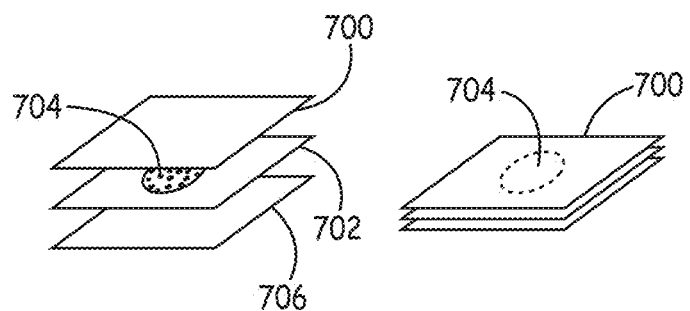
FIG. 7 is an exploded view of an encapsulated SAP deposit in cover sheets.
FIG. 8 is a perspective view of an encapsulated SAP deposit in cover sheets.

To confine the SAP to stay in a particular area, the SAP deposit can optionally be encapsulated, as depicted for example in FIG. 7-8. In FIG. 7-8 the absorbent sheet 702 containing the SAP Deposit 704 is sandwiched between two layers of cover sheet 700. In some embodiments, the absorbent sheet of the sheeted SAP structure can form one side of the enclosed SAP deposit. The two layers are then sealed to form a sealed SAP structure ABC. The sealing can be performed near the edges of cover sheets 700, 706 or near SAP deposit 704, depending on the desired containment and specificity of the SAP deposit. The SAP deposit may also be encapsulated in a single sheet that is molded or folded around the SAP deposit. The cover sheet beyond the sealed or laminated portion may optionally be trimmed or removed as required by the final product. At least one of cover sheets 700, 706 or portion thereof is generally permeable to aqueous liquids. A mat of coated yarn or other similar structure can be similarly encased in cover sheets for incorporation into a product.

Figures 9, 10:
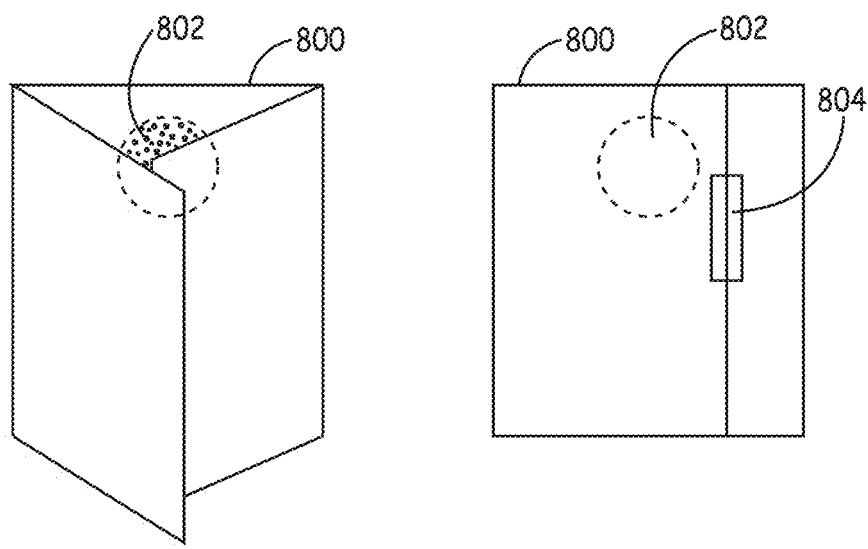
FIG. 9 is a perspective view of a processing system encapsulating a SAP deposit in a cover sheet using C-Folding.
FIG. 10 is a view of an encapsulated SAP deposit in a cover sheet using C-Folding.
Figure 11:
FIG. 11 is a photograph of a hand deposited SAP dispersion on an absorbent sheet.
Figure 12:
FIG. 12 is a photograph with an enlarged view of the hand deposited SAP dispersion on an absorbent sheet of FIG. 11.
Figure 13:
FIG. 13 is a photograph of the SAP deposit of FIG. 11 after the passage of time showing some drying of the SAP deposit.
Figure 14:
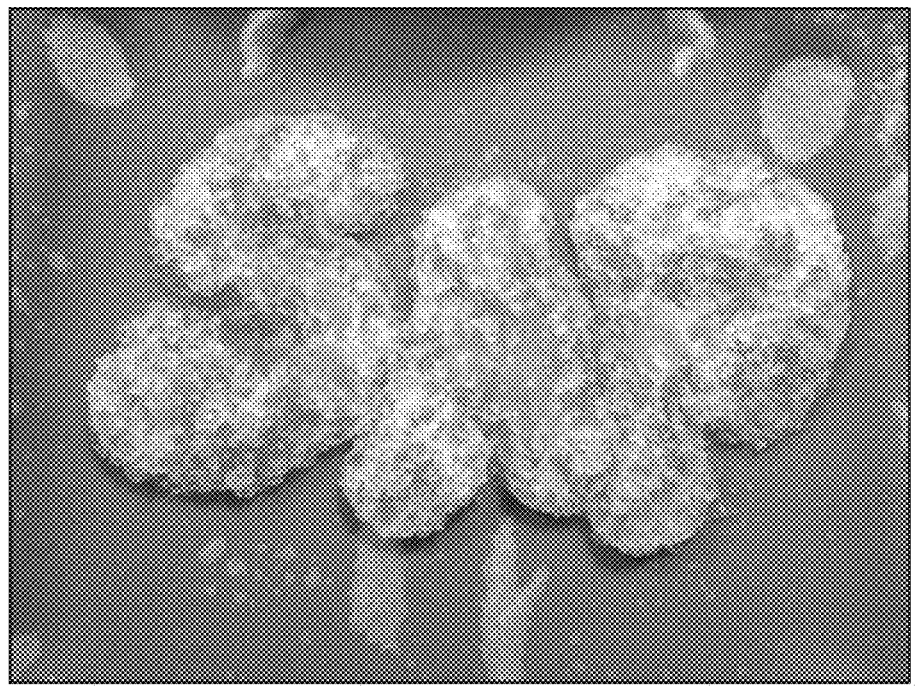
FIG. 14 is a photograph of the SAP deposit of FIG. 13 after the passage of additional time showing a deposit with greater drying.
Figure 15:
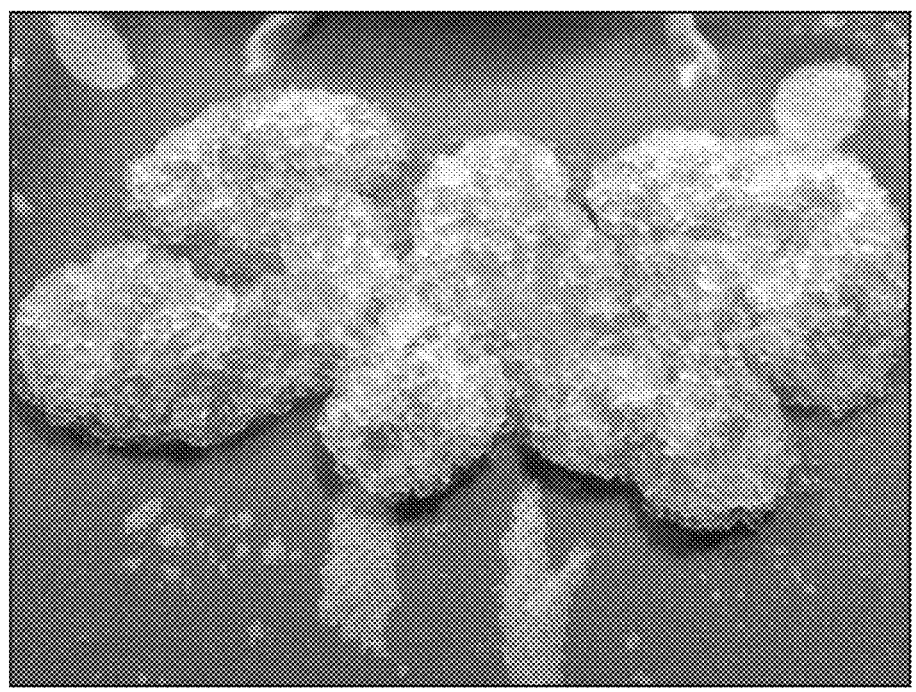
FIG. 15 is a photograph of the SAP deposit of FIG. 11 following drying.
Figure 16:
FIG. 16 is a photograph of an enlarged view of the dried SAP deposit of FIG. 15.

The SAP can also be encapsulated by C-folding, as depicted for example in FIGS. 9-10. In FIG. 10 absorbent sheet 800 containing SAP deposit 802 is folded over itself in an overlapping manner, and FIG. 9 depicts sheet 800 partially folded before the folding process is complete. To prevent absorbent sheet 800 from unfolding, the absorbent sheet can be optionally secured by tape 804.

The absorbent sheet, the SAP deposit, and the optional encapsulating cover sheet are then incorporated in to the final product. The final product may optionally include, backing sheets, additional cover sheets, top covers, padding, or other structural features.

EXAMPLES

Figure 17:
FIG. 17 is a photograph of a dried SAP deposit on an absorbent sheet.
Figure 18:
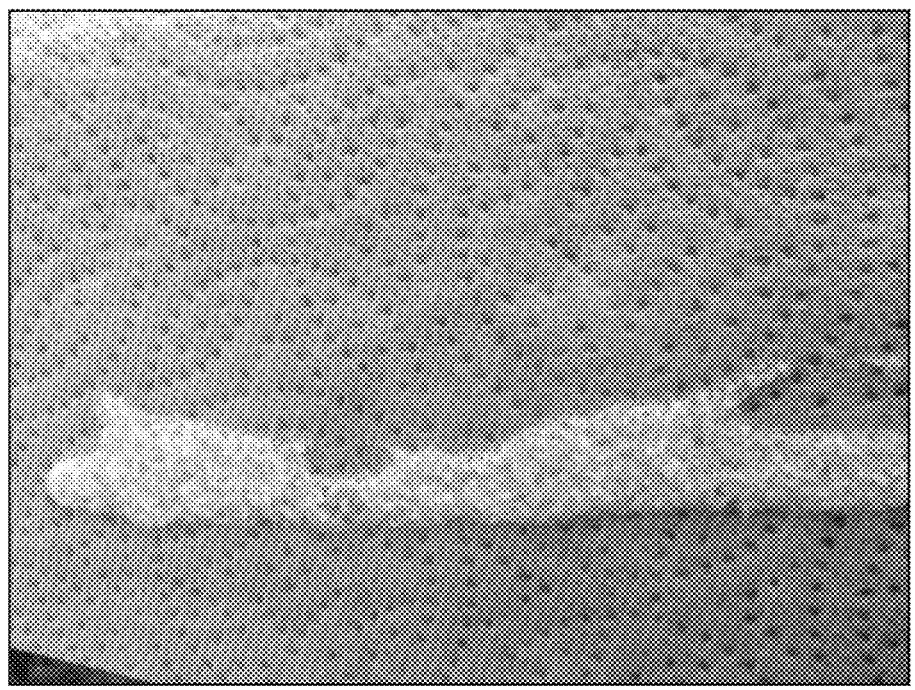
FIG. 18 is a photograph with an enlarged view of the dried SAP deposit on an absorbent sheet of FIG. 17.

A dispersion was formed by adding 20 weight percent sodium polyacrylate (Stockhausen) in PEG 400 (Dow). The dispersion was mixed well by hand to form a thick paste. The paste was deposited by hand with a 60 cc syringe to write out "SAP" on a sheet of tissue with a thickness of roughly several millimeters. The paste was then allowed to dry over a time period of roughly 5 minutes. A series of photographs showing the sheeted SAP as deposited and then over the course of the drying period is shown in FIGS. 11-16. Another embodiment of a sample of deposited and dried SAP is also depicted in FIGS. 17-18. The SAP polymer spread modestly during the drying process. As deposited, the material looked very pasty, but following the drying process, the material looked granular reflecting the particulate aspect of the SAP polymer.

The dried sheeted SAP was shaken by hand moderately vigorously, and only a very small fraction of the material separated from the structure as a powder. This indicates that the dried deposits are stable on the porous sheet. The dried deposits felt dry to the touch. Water was slowly introduced to the sheet in a tray of water. The SAP deposit swelled with water as would be expected for the granular polymer material, and even with the swelling the swelled polymer stayed in position on the sheet submerged in the water.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

What is claimed is:

1. A blend comprising: superabsorbent polymer (SAP) and at least about 15 weight percent polyol that is liquid at or above 65° C., wherein the SAP is dispersed in a matrix of the polyol and wherein the blend comprises at least about 85 weight percent of SAP and polyethylene glycol (PEG) combined.

2. The blend of claim 1 wherein the polyol is a liquid at room temperature and wherein the blend is a room temperature flowable composition.

3. The blend of claim 1 wherein the blend is a solid at room temperature and has a melting point of no more than about 65° C.

4. The blend of claim 1 wherein the SAP comprises salts of polyacrylic acid and wherein the polyol is polyethylene glycol.

5. The blend of claim 1 comprising from about 5 weight percent SAP to about 85 weight percent SAP.

6. The blend of claim 5 where in the polyethylene glycol has an average molecular weight of no more than about 800 g/mol.

7. The blend of claim 1 comprising at least about 45 weight percent polyether polyol and superabsorbent polymers with prior to dispersion an average particle size from about 10 microns to about 250 microns and an absorption of at least about 8 weight percent of aqueous (0.9 weight % sodium chloride) solution.

8. A method of making a water absorbent article, the method comprising: flowing a water absorbent composition onto an absorbent sheet along a surface at a selected location to form a deposit along a fraction of the sheet surface, wherein the water absorbent composition comprises at least about 5 weight percent super absorbent polymer and at least about 25 weight percent polyol, wherein the combined superabsorbent polymer and polyol makes up at least 85 weight percent of the water absorbent composition.

9. The method of claim 8 wherein the water absorbent composition is at a temperature of at least about 35° C.

10. The method of claim 8 wherein the water absorbent composition is at room temperature.

11. The method of claim 8 wherein the flowing of the water absorbent composition comprises spraying the water absorbent composition.

12. The method of claim 8 wherein the flowing of the water absorbent composition comprises extruding the water absorbent composition.

13. The method of claim 8 wherein the absorbent sheet is dispensed from a dispensing roll.

14. The method of claim 8 further comprising heating the water absorbent composition after it has been flowed onto the transfer sheet.

15. The method of claim 8 further comprising removing a substantial portion of the polyol to form a dried absorbent deposit wherein the dried absorbent deposit has a water absorbing capability at least about 50% of the super absorbent polymer component.

16. The method of claim 15 wherein the removal of the polyol comprises wicking the polyol into the absorbent sheet.

17. The method of claim 15 further comprising encasing the dried absorbent deposit with a cover sheet.

18. A water absorbent product comprising a first sheet having a top surface, a second sheet having a bottom surface oriented toward the top surface of the first sheet, and a water absorbent composition comprising superabsorbent polymer localized to cover a portion of the second sheet wherein the superabsorbent polymer forms a water absorbent deposit, secured between the first sheet and the second sheet and in contact with the top surface and the bottom surface wherein a seam is formed between the top surface and the bottom surface to form a sealed enclosure that encloses the water absorbent deposit and wherein the water absorbent composition comprises at least about 75 weight percent superabsorbent polymer and has a water absorption capacity of at least about 4 grams of water per gram of composition.

19. The water absorbent product of claim 18 wherein the interface between the water absorbent deposit and the sheets is free of adhesive.

20. The water absorbent product of claim 18 wherein the water absorbent composition has an average thickness of at least about 5 mm relative to the bottom sheet surface.

21. The water absorbent product of claim 18 further comprising a polyol absorbed onto the second sheet.

22. The water absorbent product of claim 18 wherein the water absorbent composition further comprises two localized superabsorbent polymer areas.

23. The water absorbent product of claim 18 wherein the water absorbent composition covers between about 10% to about 90% of the second sheet.

24. The water absorbent product of claim 18 wherein the water absorbent composition is from about 0.1 mm to about 2 cm thick.

\* \* \* \* \*